US00PP13864P39

(12) United States Plant Patent
Bunnik

(10) Patent No.: US PP13,864 P3
(45) Date of Patent: Jun. 3, 2003

(54) GUZMANIA PLANT NAMED 'DEPLAGNUM'

(76) Inventor: Ronald Bunnik, Hoefslag 3, 2641 ZZ, Pijnacker (NL)

( * ) Notice: Subject to any disclaimer, the term of this patent is extended or adjusted under 35 U.S.C. 154(b) by 0 days.

(21) Appl. No.: 10/004,347

(22) Filed: Dec. 6, 2001

(65) Prior Publication Data

US 2002/0199230 P1 Dec. 26, 2002

(30) Foreign Application Priority Data

Apr. 25, 2001 (EP) ..... 2001/0626

(51) Int. Cl.[7] ..... A01H 5/00

(52) U.S. Cl. ..... Plt./371

(58) Field of Search ..... Plt./371

*Primary Examiner*—Kent Bell

(74) *Attorney, Agent, or Firm*—Foley & Lardner

(57) ABSTRACT

A new and distinct Guzmania plant named 'Deplagnum' characterized by big inflorescence size; purple inflorescence with yellow-green scape bract tips; flat top of inflorescence; and dark, wide green leaves.

2 Drawing Sheets

Latin name of the genus and species of the plant claimed: Guzmania hybrid.

Variety denomination: 'Deplagnum'.

BACKGROUND OF THE INVENTION

The present invention comprises a new and distinct cultivar of Guzmania plant, hereinafter referred to by the cultivar name 'Deplagnum'. The genus Guzmania is a member of the family Bromeliaceae.

Guzmania comprise a genus of over 100 species of herbaceous evergreen perennials suitable for cultivation in the home or under glass. Guzmania are predominantly epiphytic with a few terrestrial species and are native to the tropics. For the most part the species vary in diameter from 7 or 8 inches to 3 or 4 feet and have rosettes of glossy, smooth edged leaves.

Floral bracts of Guzmania frequently have brilliant colors and may last for many months. The range of flower colors for Guzmania is generally from yellow through orange but may also include flame red and red-purple. White or yellow, tubular, three petalled flowers may also appear on a stem or within the leaf rosette but are usually short lived.

Guzmania may be advantageously grown as potted plants for greenhouse or home use. Desirably the plants are shaded from direct sunlight during the spring to autumn period, the central vase-like part of the leaf rosette is normally filled with water.

Guzmania is native to tropical America. Leaves of the Guzmania are usually formed as basal rosettes which are stiff and entire and in several vertical ranks. Guzmania have terminal spikes or panicles which are often bracted with petals united in a tube about as long as the calyx.

Asexual propagation of Guzmania is frequently done through the use of tissue culture practices. Propagation can also be from off-shoots which are detached from the mother plant, and may be grown in an appropriate soil or bark mixture.

The new cultivar 'Deplagnum' is the product of a planned breeding program and originated by the inventor Ronald Bunnik, in 1995 in Pijnacker, The Netherlands. The instant plant was a naturally occurring branch mutation of an unnamed Guzmania plant. The selection comprising the new variety was chosen after commencement of flowering in 1995.

The new cultivar was asexually propagated by taking cuttings by the inventor in Pijnacker, The Netherlands in 1995. Asexual propagation by tissue culture was initiated in 1999 by Deroose Plants, in Evergem, Belgium. Continuous asexual propagation has demonstrated that the combination of characteristics as herein disclosed for the new cultivar 'Deplagnum' are firmly fixed and are retained through successive generations of asexual reproduction. The new cultivar reproduces true to type.

BRIEF DESCRIPTION OF THE INVENTION

The following traits have been repeatedly observed and are determined to be basic characteristics of 'Deplagnum' which in combination distinguish this Guzmania as a new and distinct cultivar:

1. Big inflorescence size;
2. Purple inflorescence with yellow-green scape bract tips;
3. Flat top inflorescence;
4. Dark and wide green leaves 'Deplagnum' has not been observed under all possible environmental conditions. The phenotype of the new cultivar may vary significantly with variations in environment such as temperature, light intensity, and day length without any change in genotype.

Of the many commercial cultivars known to the present inventor, the most similar in comparison to 'Deplagnum' is the Guzmania cultivar 'Indian' (unpatented). In comparison to 'Indian', the inflorescence of 'Deplagnum' is flatter on the top, is much bigger and darker colored. Guzmania 'Deplagnum' also has darker green and wider leaves than 'Indian'. The flower shape of 'Deplagnum' is more compact than the flower shape of 'Indian'. 'Deplagnum' differs from its parent primarily in bract coloration.

BRIEF DESCRIPTION OF THE DRAWING

The accompanying photographic illustration shows a 19-month-old 'Deplagnum' plant following growth under appropriate growing conditions, with colors being as true as possible with illustrations of this type.

The drawing at the top of sheet one depicts a side view of the plant.

The drawing at the bottom of sheet one depicts a close up of the inflorescence.

The drawing on sheet two depicts a close up side view of the plant.

DEAILED BOTANICAL DESCRIPTION

The following observations, measurements and values describe 19 month old plants grown in 12 cm containers in Pijnacker, The Netherland under greenhouse conditions which closely approximate those generally used in horticultural practice. 'Deplagnum' is grown in a commercial greenhouse under 21 degrees Celsius day and night. No artificial lighting or photoperiodic treatments are conducted but 'Deplagnum' is forced into flowering by adding acetylene. Highest temperature resistance is 40 degrees Celsius, the lowest 5 degrees Celsius. Direct sunlight has to be avoided because it causes burning of the leaves. The following fertilizer is added: 1 part nitrogen, 0.5 parts phosphorus, 3 parts Kalium and 0.2 parts Magnesium. Water should not contain too much salts. From the start of tissue culture it takes five years to produce a commercial plant. The amount of time needed to produce a flower depends on the amount of acetylene is added. The flowers have a tenability of up to six months depending on the environment they are grown and kept in.

Color references are made to The Royal Horticultural Society Colour Chart (R.H.S.), except where general colors of ordinary significance are used.

Propagation: Tissue culture.

Plant:

*Form.*—Upright, leaves in basal rosette.

*Height.*—Average 42 cm.

*Diameter.*—Average 50 cm.

*Growth habit.*—Upright, growth moderate.

Foliage:

*Size.*—Leaves have an average length of 31 cm and an average width of 4 cm (measured at the middle of a leaf).

*Shape.*—Linear, tips acute.

*Margin.*—Entire.

*Surface texture.*—Smooth, glossy.

*Color.*—Leaf color upper side dark yellow-green, closest too but slightly darker than RHS 147 A. Leaf color under side yellow-green RHS 147 A.

Bracts:

*General shape/arrangement.*—Broad lanceolate, arranged alternately, tips horizontal to slightly bent downwards in an average angle of 0° (=horizontal) to 40°.

*Shape bracts.*—Number: Average 7. Length: Average 19.8 cm. Width: Average 3.8 cm. Margin: Entire. Apex: Apiculate. Texture: Smooth, glossy. Color: Upper side greyed-purple, between RHS 187 A and RHS 187 B; upper half and tips yellow-green, RHS 147 A; Under side greyed-purple, between RHS 187 B and RHS 187 C.

*Primary bracts.*—Number: Average 7. Length: Average 15.4 cm. Width: Average 3.3 cm. Margin: Entire. Apex: Apiculate. Texture: Smooth, glossy. Color: Upper side greyed-purple, RHS 187 A; tips dark yellow-green, RHS 147 A to dark greyed-purple, RHS N186A; under side greyed-purple, between RHS 187 B and RHS 187 C, with dark yellow-green tips, RHS 147 A to dark greyed-purple, RHS N186A.

*Floral bracts.*—Number: Average 12. Length: Average 9.0 cm. Width: Average 3.2 cm. Margin: Entire. Apex: Apiculate. Texture: Smooth, glossy. Color: Upper side greyed-purple, RHS 187 A; under side greyed-purple, between RHS 187 B and RHS 187 C.

Inflorescence: Inflorescences are placed in the axils of the floral bracts; on average there are 9 inflorescences with an average length of 3.1 cm; each inflorescence consists of an average of 7 individual flowers.

*Sepal.*—Each perianth consists of one large sepal, narrow oblong shape, slightly folded, average length 2.6 cm, average width 9 mm, outside color yellow-green, RHS 151 B with yellow-orange tip RHS 16 A, lighter base, RHS 151 C; inner side yellow-green, RHS 151 with yellow-orange tip; RHS 16 A, lighter base; RHS 151 C.

*Petals.*—6, linear, 3 outer petals have an average length of 2.4 cm and an average width of 4 mm, green-white in color, RHS 157 A on both surfaces with yellow tips, RHS 6 D; 3 inner petals have an average length of 2 cm and an average width of 4 mm, yellow-orange in color, RHS 16 A on both surfaces, lighter yellow base, between RHS 12 B and RHS 12 C.

*Calyx.*—Average width 6 mm.

Reproductive organs:

*Stamens.*—6, attached to the base of the inner 3 petals.

*Anthers.*—Yellow, RHS 4 D; produce small quantity of light yellow pollen, between RHS 4 C and RHS 4 D.

*Style.*—Each individual flower holds one style, average length 1.5 cm, yellow RHS 7 B.

*Stigma.*—Average length 2 mm, split into 3 clavate parts.

Seed characteristics: No fruits or seeds observed to date.

Roots: Thin, very well-branched, strong to moderately strong, color brown RHS 199 C.

Disease/pest resistance/susceptibility: 'Deplagnum' is no more susceptible or resistant to disease and pests than other Guzmania varieties.

I claim:

1. A new and distinct Guzmania plant named 'Deplagnum' as described and illustrated herein.

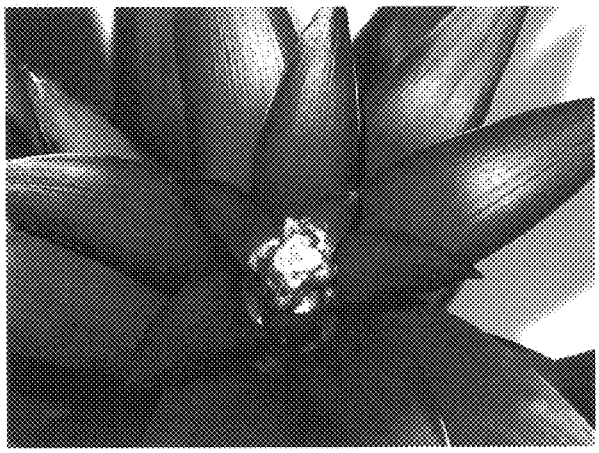
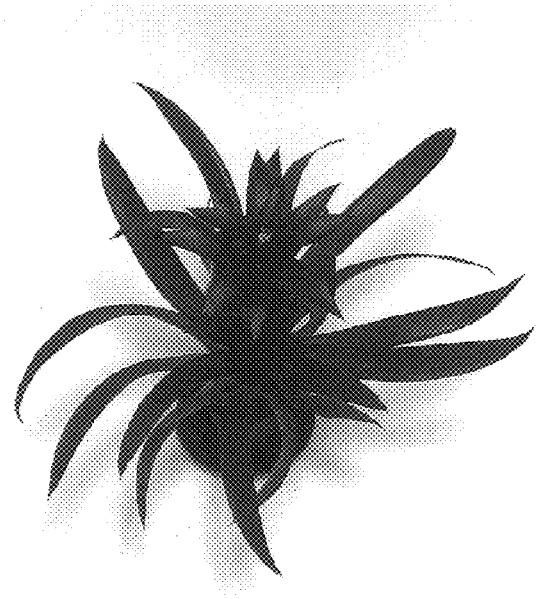

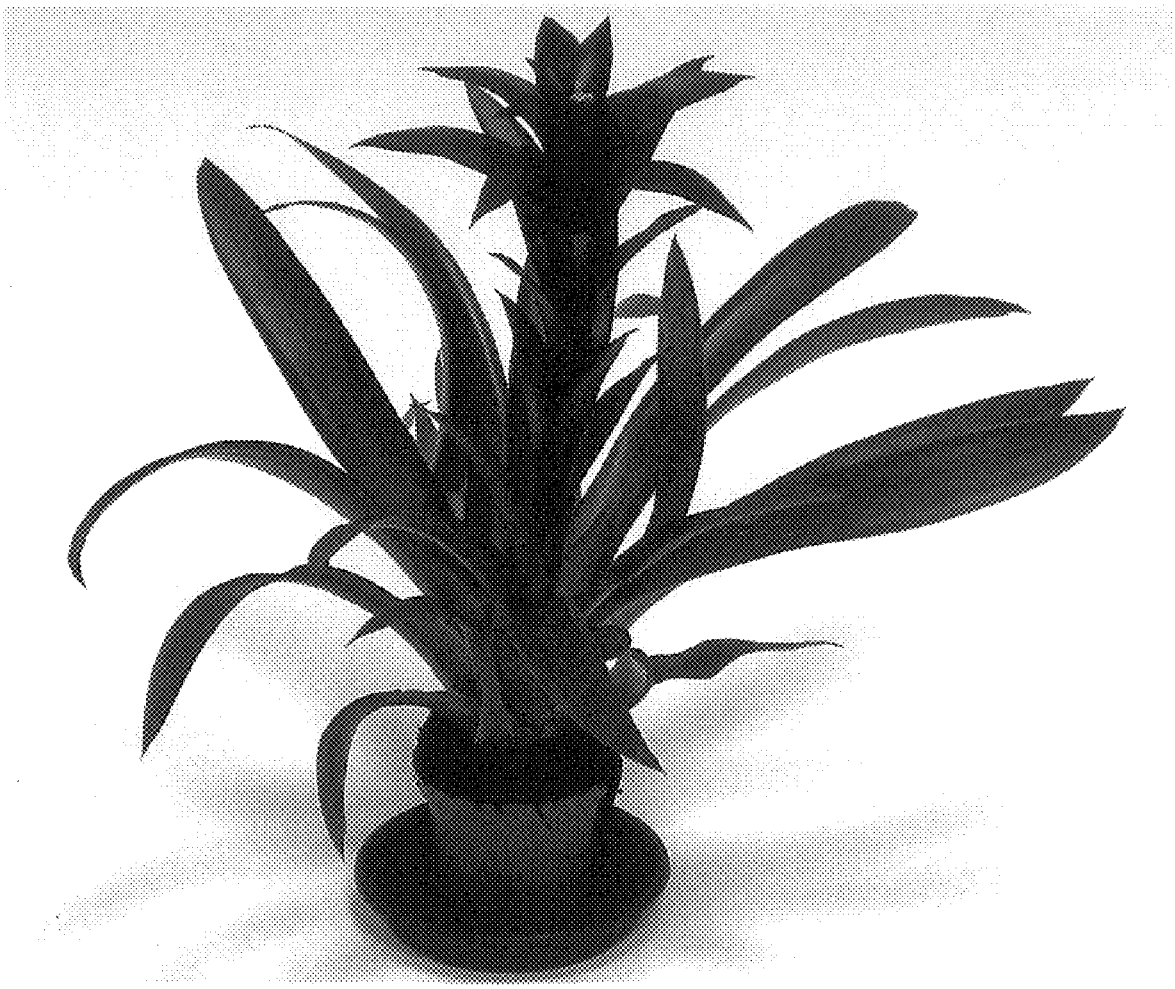

* * * * *